United States Patent [19]
Kaetsu et al.

[11] Patent Number: 5,811,279
[45] Date of Patent: Sep. 22, 1998

[54] METHOD FOR ACTIVATING PROTHROMBIN WITH POLYETHYLENE GLYCOL

[75] Inventors: Hiroshi Kaetsu; Jun Mizuguchi; Takayoshi Hamamoto, all of Kumamoto, Japan

[73] Assignee: Juridical Foundation The Chemo-Sero-Therapeutic Research Institute, Kumamoto, Japan

[21] Appl. No.: 905,041

[22] Filed: Aug. 1, 1997

[30] Foreign Application Priority Data

Aug. 9, 1996 [JP] Japan .................................. 8-227695

[51] Int. Cl.$^6$ .............................. C12N 9/74; A61K 38/48
[52] U.S. Cl. ......................................... 435/214; 424/94.64
[58] Field of Search .......................... 435/214; 424/94.64

[56] References Cited

U.S. PATENT DOCUMENTS

| | | | |
|---|---|---|---|
| 5,138,034 | 8/1992 | Uemura et al. | 530/413 |
| 5,281,528 | 1/1994 | Boctor et al. | 435/212 |
| 5,304,372 | 4/1994 | Michalski et al. | 424/94.64 |
| 5,677,162 | 10/1997 | Zou et al. | 435/214 |

FOREIGN PATENT DOCUMENTS

| | | |
|---|---|---|
| 0543178 | 10/1992 | European Pat. Off. . |
| 0541507 | 11/1992 | European Pat. Off. . |
| 0763596 | 8/1995 | European Pat. Off. . |
| 4365481 | 12/1992 | Japan . |
| 733799 | 2/1995 | Japan . |

OTHER PUBLICATIONS

Abshire et al. (1995) Blood, 86(10 Suppl. 1), "Activated Coagulation in Patients Receiving Polyethylene Glycol Conjugated L–Asparaginase (PEG–Asp)", p. 863A, Abstract No. 3438.

W. Berg et al., "The Isoelectric Point of Thrombin and Its Behaviour Compared to Prothrombin at Some Solid Surfaces", Thrombos. Haemostas., vol. 42, pp.972–982, 1979.

Ts. Tsvetkov et al., "A Method For Preparation of Dry Thrombin For Topical Application", Cryobiology, vol. 21, pp. 661–663, 1984.

S. Le Borgne et al., "Amidase Activity and Thermal Stability of Human Thrombin", Applied Biochemistry and Biotechnology, vol. 48, pp. 125–135, 1994.

M.P. McGee et al., "Protein Hydration During Generation of Coagulation Factor Xa in Aqueous Phase and on Phospholipid Membranes", The Journal of Biological Chemistry, vol. 270, No. 25, pp. 15170–15174, Jun. 23, 1995.

*Primary Examiner*—Jon P. Weber
*Attorney, Agent, or Firm*—Browdy and Neimark

[57] ABSTRACT

A method for activating prothrombin to thrombin is presented which comprises treating an aqueous solution containing prothrombin with polyethylene glycol in the presence or absence of the calcium salt. The method enables conversion of prothrombin to thrombin in the absence of thromboplastin and allows for preparation of thrombin on an industrially large scale from easily available starting materials.

20 Claims, 14 Drawing Sheets

METHOD FOR ACTIVATING PROTHROMBIN WITH POLYETHYLENE GLYCOL

The present invention relates to a method for preparing thrombin. More particularly, the present invention relates to a method for activating prothrombin to thrombin by treating an aqueous solution containing prothrombin with polyethylene glycol in the presence or absence of the calcium salt and in the absence of thromboplastin to allow for industrially large scale of production of thrombin from easily available starting materials.

PRIOR ART

Thrombin, a serine protease having a molecular weight of about 37,000, is a proteinase which acts at the final stage of blood coagulation and coagulates blood by converting fibrinogen into fibrin. Thus, thrombin has been clinically employed as a local hemostatic in the surgical region or as a hemostatic for hemorrhage in the upper intestinal tract in the internal medical region. Thrombin is also used as a component of a fibrin adhesive.

In the circulating blood, a precursor prothrombin occurs which is subjected to restricted degradation with activated Factor X to form thrombin. Hitherto, thrombin has been prepared by first extracting and purifying prothrombin from human or bovine plasma and then treating the purified prothrombin thus obtained with, for example, thromboplastin to form thrombin. That is, it was a purified prothrombin that is converted into thrombin. The thus obtained thrombin is further purified with several various procedures. An improved process of this procedure is also known wherein plasma is treated with cold ethanol and then with an anion exchanger and the purified prothrombin thus obtained is converted into thrombin, which is purified with a cation exchanger (see Japanese Patent Publication No. 128398/1991).

Thromboplastin used for conversion of prothrombin into thrombin has been obtained from human placenta. This starting material, human placenta, however, is hardly available, and hence, thromboplastin is difficult to obtain in a large quantity. Furthermore, thromboplastin cannot completely be removed during the manufacturing process and thus a final product is likely to be contaminated with this protein.

In addition to the use of thromboplastin as described above, there have been known a number of processes for conversion of prothrombin into thrombin, including conversion with snake venom, or with a high concentration of a citrate (Japanese Patent Publications No. 365481/1992, and No. 194261/1993), and the like. However, snake venom is also hardly available and a final product might possibly be contaminated with venom like in the case of thromboplastin. Although natural conversion with a high concentration of a citrate is advantageous in that there is no risk for contamination of a final product with a tissue protein such as thromboplastin, a conversion rate is not sufficiently high in industrial point of view.

Conversion of prothrombin into thrombin using calcium chloride has been disclosed in Japanese Patent Publications No. 186369/1993, No. 46852/1994, and International Patent Publication WO 95/31536. Japanese Patent Publication No. 33799/1995 discloses conversion of prothrombin complex instead of purified prothrombin into thrombin.

The procedures as described above can effectively be used for production of thrombin under merely restricted conditions but still do not attain requirements of simplicity and effectiveness.

SUMMARY OF THE INVENTION

Under the circumstances, the present inventors have intensively studied in order to establish a process for efficiently preparing thrombin on an industrially large scale, and as a result, have found that thrombin can be prepared from prothrombin in the absence of thromboplastin using easily available starting materials by treating an aqueous solution containing prothrombin with polyethylene glycol in the presence or absence of a calcium salt.

The object of the present invention is to provide a method for activating prothrombin to thrombin which comprises treating an aqueous solution containing prothrombin with polyethylene glycol in the presence or absence of a calcium salt.

Another object of the present invention is to provide a method for activating prothrombin to thrombin which comprises treating an aqueous solution containing prothrombin with polyethylene glycol in the presence or absence of a calcium salt and in the presence of glycerol.

Still another object of the present invention is to provide a method for preparing thrombin which comprises activating prothrombin to thrombin by the method as described above and isolating thrombin thus obtained.

Further object of the present invention is to provide the method for preparing thrombin as described above which further comprises treating the isolated thrombin with a cation exchanger for purification.

These and other objects and advantages of the invention will be apparent to those skilled in the art from the following description.

DETAILED DESCRIPTION OF THE INVENTION

The present invention provides a method for activating prothrombin to thrombin even in the absence of thromboplastin as well as a method for preparing thrombin by utilizing said method for activation.

In a preferred aspect of the present invention, "prothrombin complex" or "an aqueous solution containing mainly prothrombin and blood coagulation Factor X" is used for conversion into thrombin. As used herein, the term "prothrombin complex" is referred to as a mixture of prothrombin (blood coagulation Factor II; a member of blood coagulation factors), with another factors involved in blood coagulation, including blood coagulation Factor VII, Factor IX, Factor X, and the like. Materials to be subjected to conversion need not be a highly purified product but may be a crude product.

Starting materials "prothrombin complex" or "an aqueous solution containing mainly prothrombin and blood coagulation Factor X" may be prepared by various procedures, including treatment of plasma with an anion exchanger to prepare prothrombin complex, production of prothrombin from cryoprecipitate-poor plasma which is prepared by removing cryoprecipitate from plasma, and the like. Starting plasma may also be derived from sources of any animal species, including bovine or human, preferably human.

The thus obtained "prothrombin complex" or "an aqueous solution containing mainly prothrombin and blood coagulation Factor X" is then treated with polyethylene glycol with or without a calcium salt at 4° to 37° C., preferably at 10° to 25° C., to activate prothrombin to thrombin. Prothrombin is used in a reaction mixture at a concentration ranging from around 20 to 120 Units/ml. Treatment of prothrombin with polyethylene glycol with or without a calcium salt is conducted in such a way that polyethylene glycol with or without a calcium salt is added to an aqueous solution containing mainly prothrombin and blood coagulation Factor X while stirring to activate prothrombin to thrombin. Specifically, a solution of polyethylene glycol with or without a calcium salt is added to an aqueous solution containing mainly prothrombin and blood coagulation Factor X and, after stirring, the mixture is left to stand, or alternatively, solid polyethylene glycol with or without solid calcium salt is directly added to an aqueous solution containing mainly prothrombin and blood coagulation Factor X and, after stirring, the mixture is left to stand. The former procedure using materials in liquid is preferred.

Polyethylene glycol having a molecular weight of about 2,000 to 6,000 is preferably used at a concentration ranging from around 1 to 30% (w/v). Polyethylene glycol as used herein is a polymer having a high molecular weight which is widely used as a precipitating agent for a protein. Polyethylene glycol must be non-toxic. Preferably, PEG 4,000 having a mean molecular weight of about 4,000 is used. A calcium salt includes, for example, calcium chloride, calcium hydroxide, calcium acetate, and the like. A calcium salt is used at a concentration of 100 mM or less, preferably at around 2 to 20 mM. Treatment may be carried out for around 1 to 7 days, which may vary as the composition of the reaction mixture is altered. In a preferred aspect of the present invention, glycerol is added to a reaction mixture. A high concentration of glycerol stabilizes thrombin formed by the activation and represses inactivation of thrombin via autolysis, thereby providing thrombin production at a high yield.

As described above, a method for preparing thrombin which comprises treating prothrombin with a calcium salt to convert into thrombin has been disclosed in Japanese Patent Publications No. 186369/1993, No. 46852/1994, and International Patent Publication WO 95/31536. However, there have been no evidences which demonstrate that activation of prothrombin to thrombin is much enhanced by treating prothrombin with polyethylene glycol in the presence of a calcium salt. Furthermore, activation of prothrombin to thrombin by treatment with polyethylene glycol in the absence of a calcium salt is quite novel. Thus, the present invention provides novel findings quite distinct from the conventional methods as described above both in procedures and effects. In accordance with the method of the present invention, thrombin can efficiently be prepared from prothrombin on an industrially large scale using easily available starting materials.

Thrombin obtained by the activation is purified by the known procedures, including, for example, but not limited to, treatment with a cation exchanger. Another known procedures can also be used for further purification. Thrombin thus obtained may be formulated into a pharmaceutical composition with any procedure known to a person skilled in the art wherein pharmaceutically acceptable carriers, additives, etc. are added, or conventional procedures such as sterile filtration, filling, lyophilization or heating are conducted.

The present invention is illustrated in more detail by means of the following Preparations, Examples and Experiments but should not be construed to be limited thereto.

Preparation 1

Cryoprecipitated supernatant obtained from human plasma was adsorbed to an anion exchanger resin. A fraction containing prothrombin and Factor X was eluted and pooled with a buffer containing 0.7M sodium chloride, pH 7.0. Prothrombin and Factor X were purified by polyethylene glycol fractionation wherein substances insoluble in 10% PEG 4,000 were removed.

Preparation 2

Prothrombin and Factor X as prepared in Preparation 1 were purified by Q-Sepharose chromatography. The obtained prothrombin had a purity of about 4 plasma units/A280.

Preparation 3

Prothrombin and Factor X as prepared in Preparation 1 were further purified by chromatography using DEAE-Sepharose and heparin-Sepharose and prothrombin was separated from Factor X. The obtained prothrombin had a purity of about 6.5 plasma units/A280.

Experiment 1

To prothrombin 22.8 plasma units/ml as prepared in Preparation 3 were added Factor X (120.5 $\mu$g/ml), 1 mM EDTA 2Na and PEG 4,000 at various concentrations and the mixture was reacted at 25° C., pH 7.4. Activity of thrombin formed was measured at each fixed time using TESTZYM$^R$ chromogenic substrate S-2238 (CHROMOGENIX AB, Sweden) wherein the thrombin activity is indicated in the NIH unit in accord with the unit of U.S. Standard Thrombin. An activation rate was used to indicate a thrombin activity (NIH unit) obtained per 1 plasma unit of prothrombin (1 plasma unit of prothrombin=prothrombin activity contained in 1 ml of normal plasma).

Figure 1:
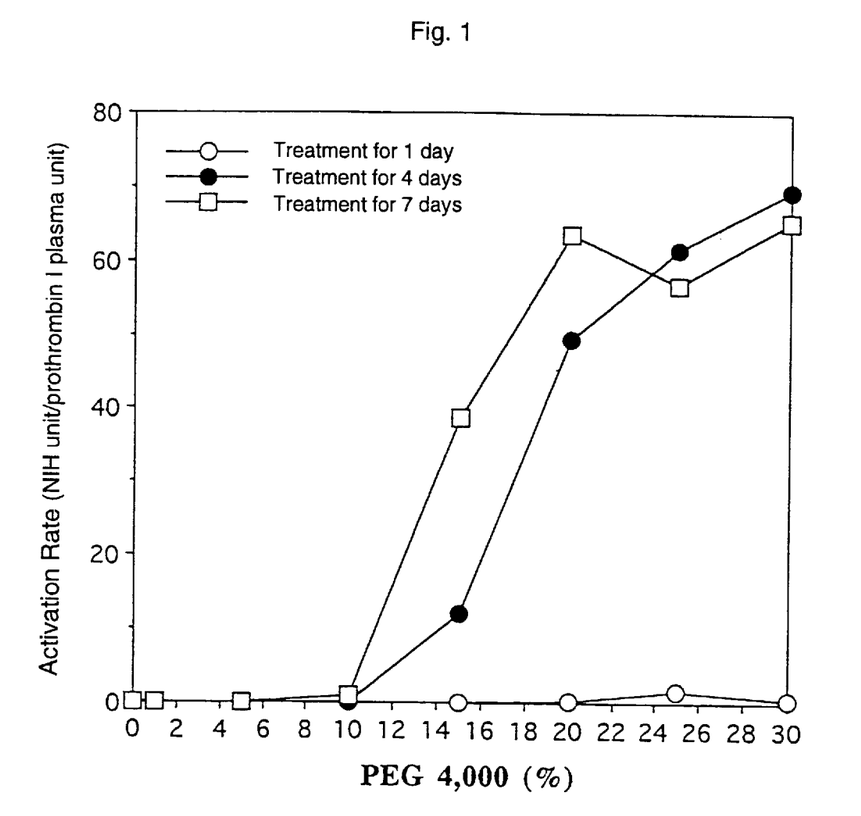
FIG. 1 shows effects of PEG 4,000 on the activation of prothrombin to thrombin in the absence of calcium chloride.

The results are shown in FIG. 1 in which activation of prothrombin was enhanced with PEG at the concentration of 15% or more.

Experiment 2

Figure 2:
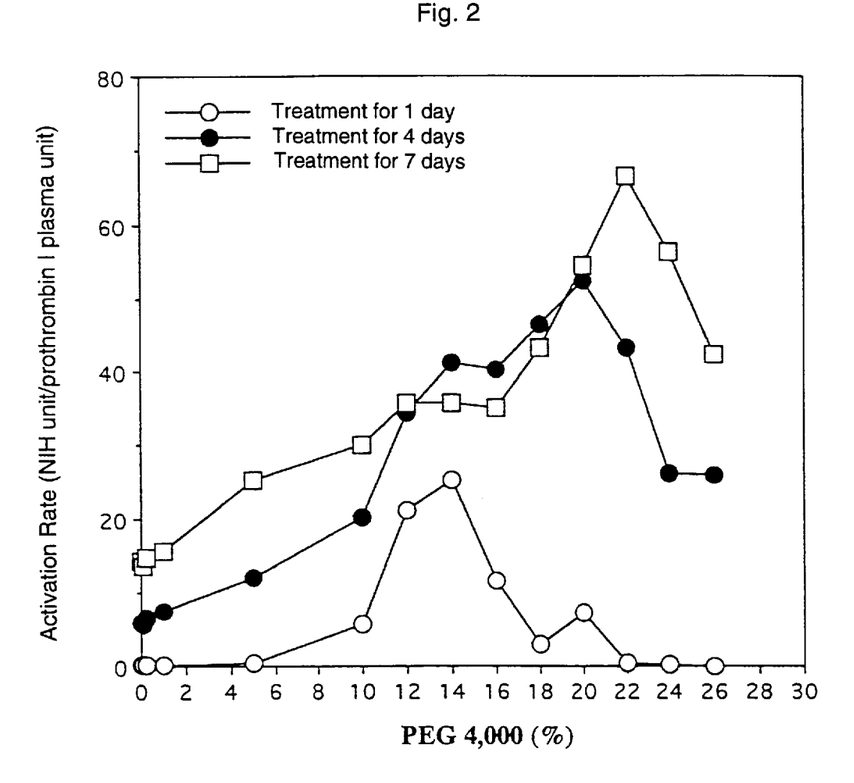
FIG. 2 shows effects of PEG 4,000 on the activation of prothrombin to thrombin in the presence of 5 mM calcium chloride.

To prothrombin 22.8 plasma units/ml as prepared in Preparation 3 were added Factor X (120.5 μg/ml), 5 mM calcium chloride and PEG 4,000 at various concentrations and the mixture was reacted at 25° C., pH 7.4. Activation rate of prothrombin to thrombin at each fixed time is shown in FIG. 2.

Enhancement of activation was proved with PEG at the concentration of 1% or more as compared to the absence of PEG. Significant enhancement of activation was proved with PEG at the concentration of 5% or more. When treatment was conducted for 1 day, increase in the activity was most prominent in the samples treated with PEG at the concentration of 12% to 14%. In case of treatment for 4 days, radical increase in the activity was observed in the samples treated with PEG at the concentration of 18% to 20%.

Experiment 3

Figure 3:
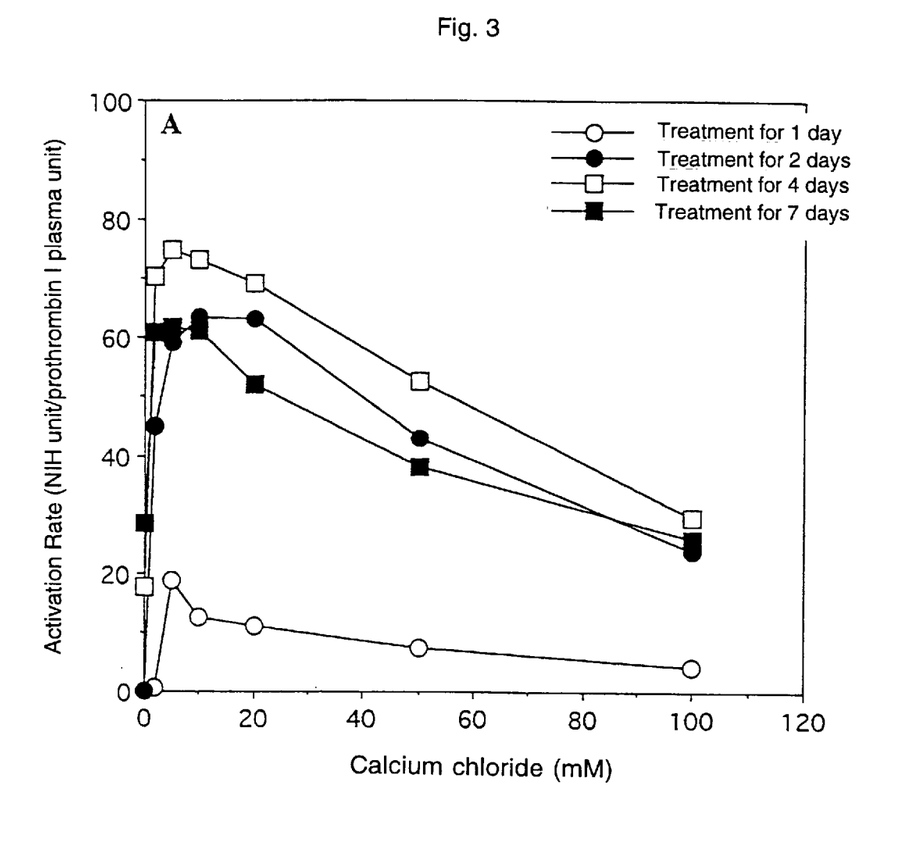
FIG. 3 shows effects of calcium chloride at various concentrations on the activation of prothrombin to thrombin in the presence of 14% PEG 4,000.
Figure 4:
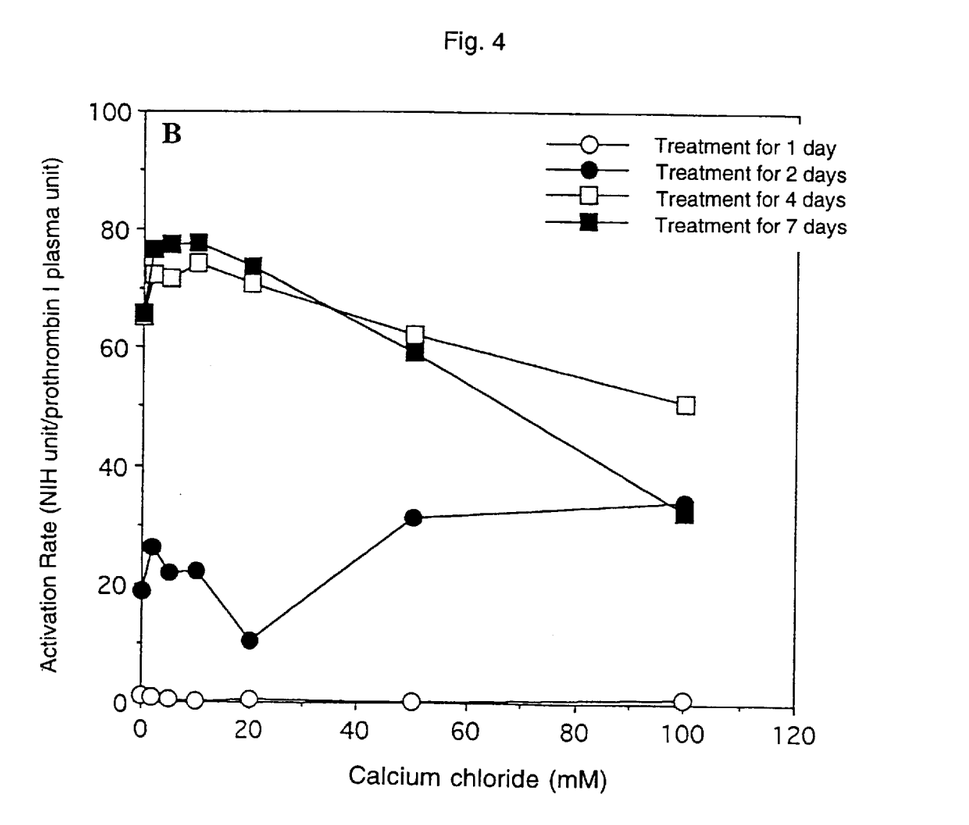
FIG. 4 shows effects of calcium chloride at various concentrations on the activation of prothrombin to thrombin in the presence of 20% PEG 4,000.
Figure 5:
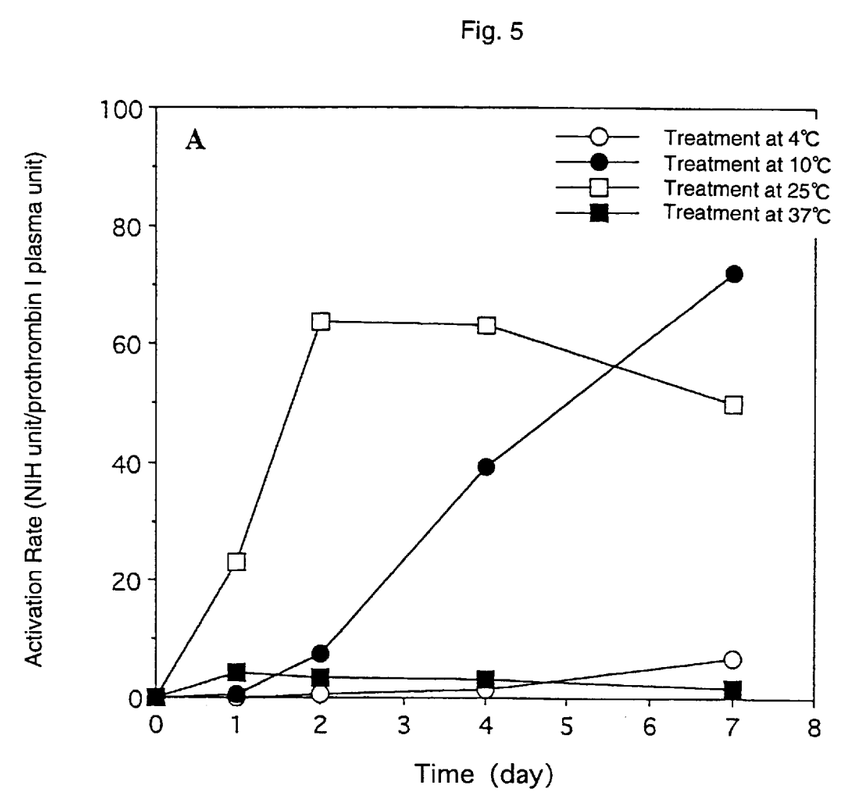
FIG. 5 shows effects of a temperature on the activation of prothrombin to thrombin in the presence of 14% PEG 4,000, depicting an activation rate after treatment for up to 7 days.
Figure 6:
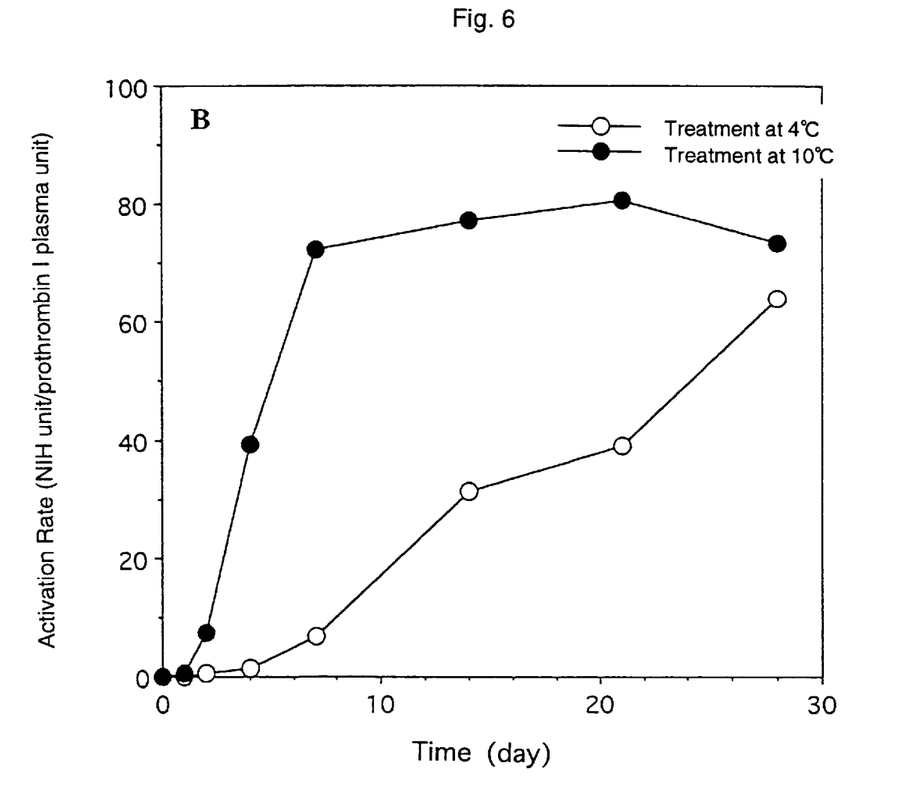
FIG. 6 shows effects of a temperature on the activation of prothrombin to thrombin in the presence of 14% PEG 4,000, depicting an activation rate after treatment for up to 28 days.
Figure 7:
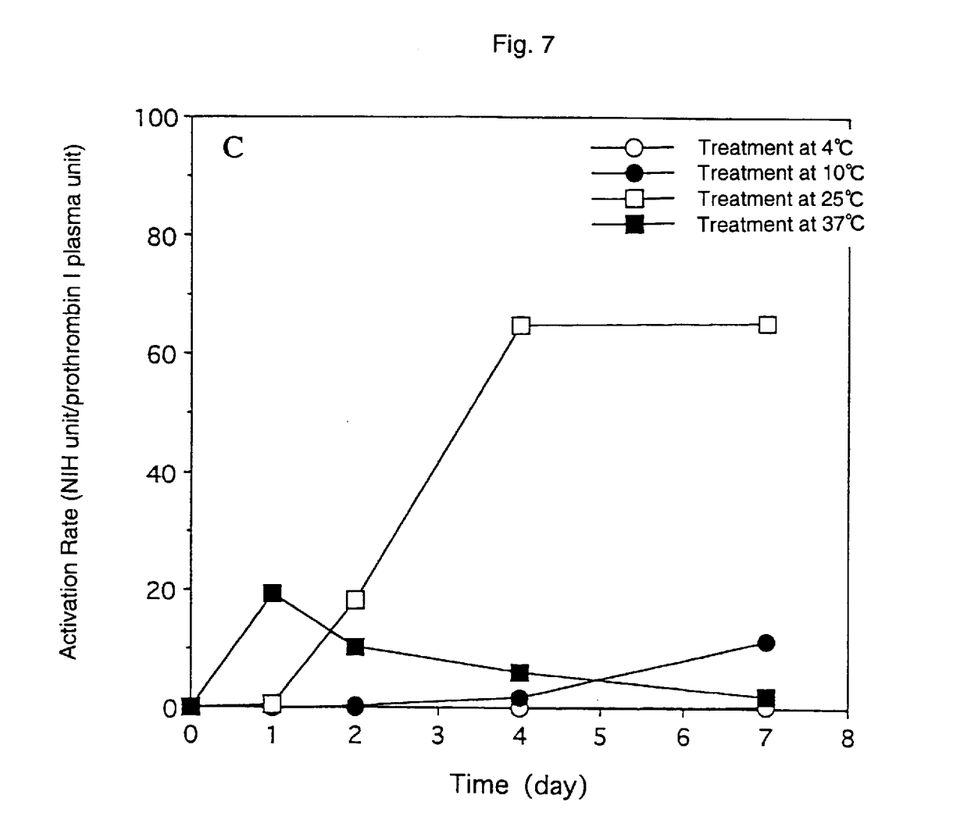
FIG. 7 shows effects of a temperature on the activation of prothrombin to thrombin in the presence of 20% PEG 4,000, depicting an activation rate after treatment for up to 7 days.
Figure 8:
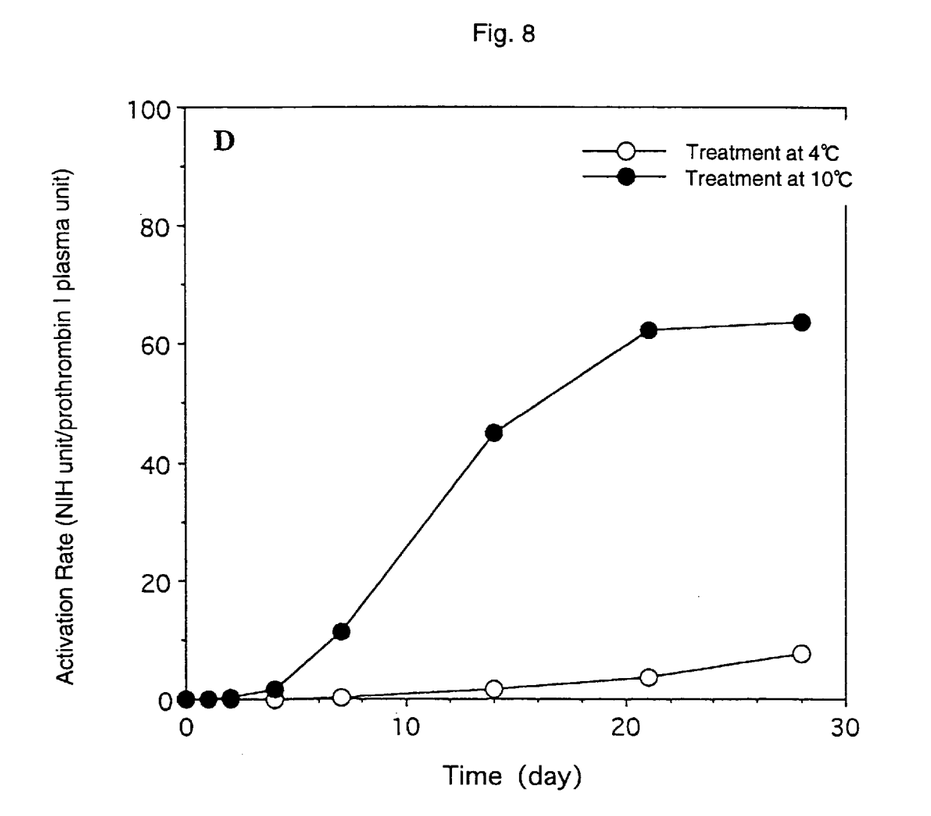
FIG. 8 shows effects of a temperature on the activation of prothrombin to thrombin in the presence of 20% PEG 4,000, depicting an activation rate after treatment for up to 28 days.

Effects of calcium chloride at various concentrations on the activation rate of prothrombin to thrombin by PEG treatment was studied. Using PEG 4,000 at the concentration of 14% or 20%, prothrombin 22.8 plasma units/ml as prepared in Preparation 3, Factor X (120.5 μg/ml) and calcium chloride at various concentrations were mixed together and the mixture was reacted at 25° C., pH 7.4. Activation rate of prothrombin to thrombin at each fixed time for 14% and 20% PEG 4,000 is shown in FIGS. 3 and 4, respectively.

With 14% PEG 4,000, significant dependency to the calcium concentration was observed with the concentration ranging from 2 to 20 mM being optimum. In case of 20% PEG 4,000, slight dependency to the calcium concentration was also observed with the concentration ranging from 2 to 20 mM being optimum.

Experiment 4

Effects of a temperature on the activation rate of prothrombin to thrombin by PEG treatment was studied. Using PEG 4,000 at the concentration of 14% or 20%, prothrombin 22.8 plasma units/ml as prepared in Preparation 3, Factor X (120.5 μg/ml) and 5 mM calcium chloride were mixed together and the mixture was reacted at the reaction temperature of 4°, 10°, 25° or 37° C., at pH 7.4. Activation rate of prothrombin to thrombin as a function of incubation time is shown in FIGS. 5 to 8.

With 14% PEG 4,000, rapid formation of thrombin was observed at 25° C. and 10° C. In case of 20% PEG 4,000, thrombin formation was also observed at 25° C. and 10° C. though slower than that with 14% PEG 4,000.

Experiment 5

Figure 9:
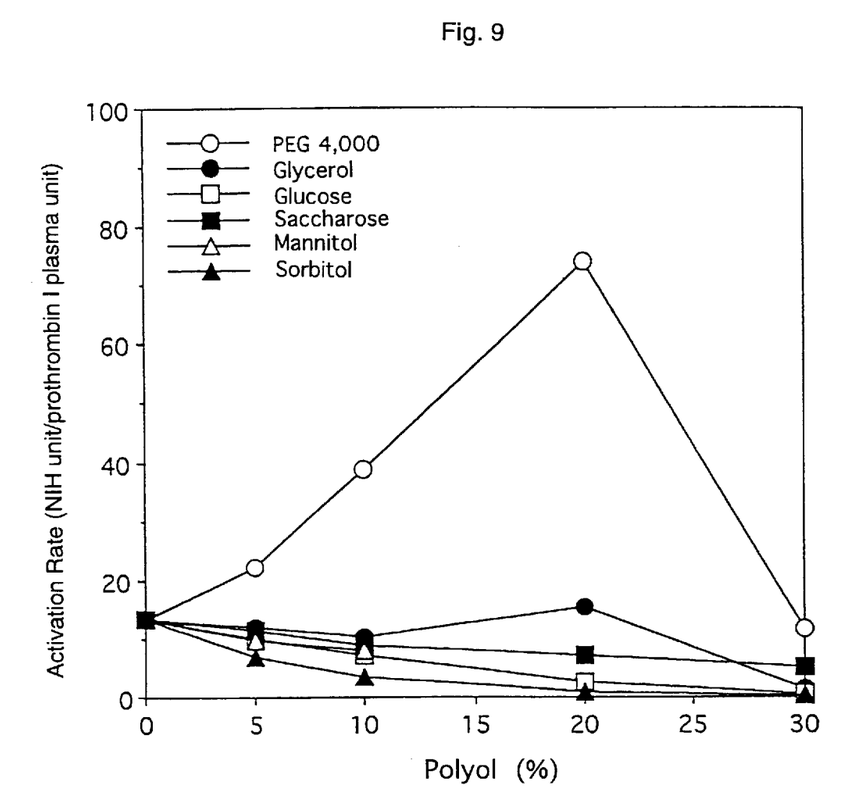
FIG. 9 shows effects of various polyols on the activation of prothrombin to thrombin, depicting an activation rate after treatment for 7 days.

Effects of PEG treatment was compared with those of addition of various polyols. With polyols at the concentration of 0%, 5%, 10%, 20% and 30%, prothrombin 22.8 plasma units/ml as prepared in Preparation 3, Factor X (120.5 μg/ml) and 5 mM calcium chloride were mixed together and the mixture was reacted at 25° C., pH 7.4. Activation rate of prothrombin to thrombin after treatment for 7 days is shown in FIG. 9.

No enhancement of activation was observed with polyols other than PEG but, on the contrary, activation was rather repressed with a higher concentration of polyols.

Experiment 6

Figure 10:
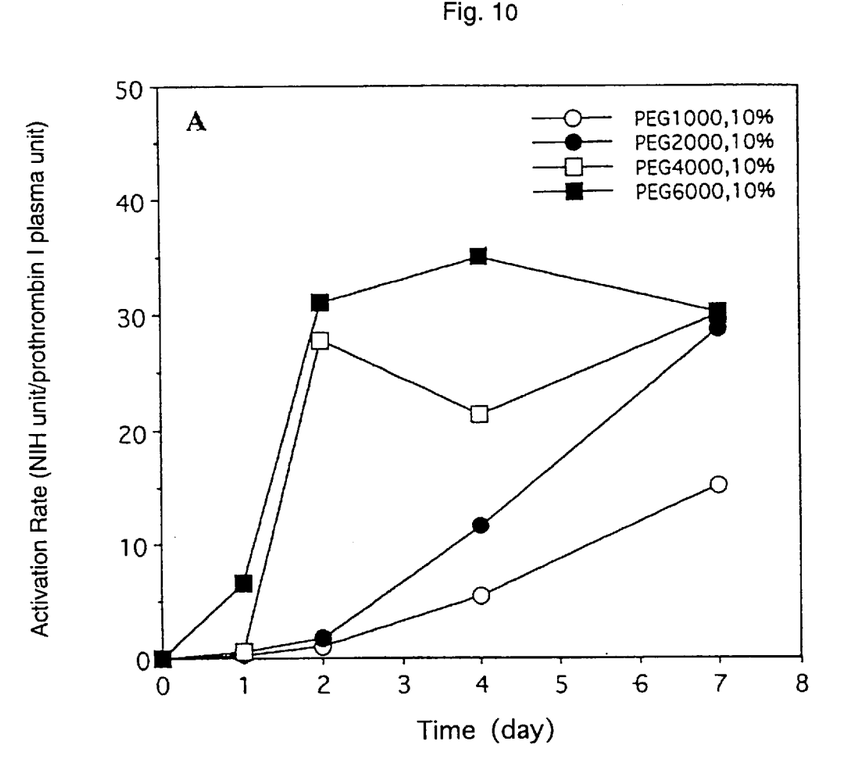
FIG. 10 shows effects of a molecular weight of PEG on the activation of prothrombin to thrombin in the presence of 10% PEG having various molecular weights.
Figure 11:
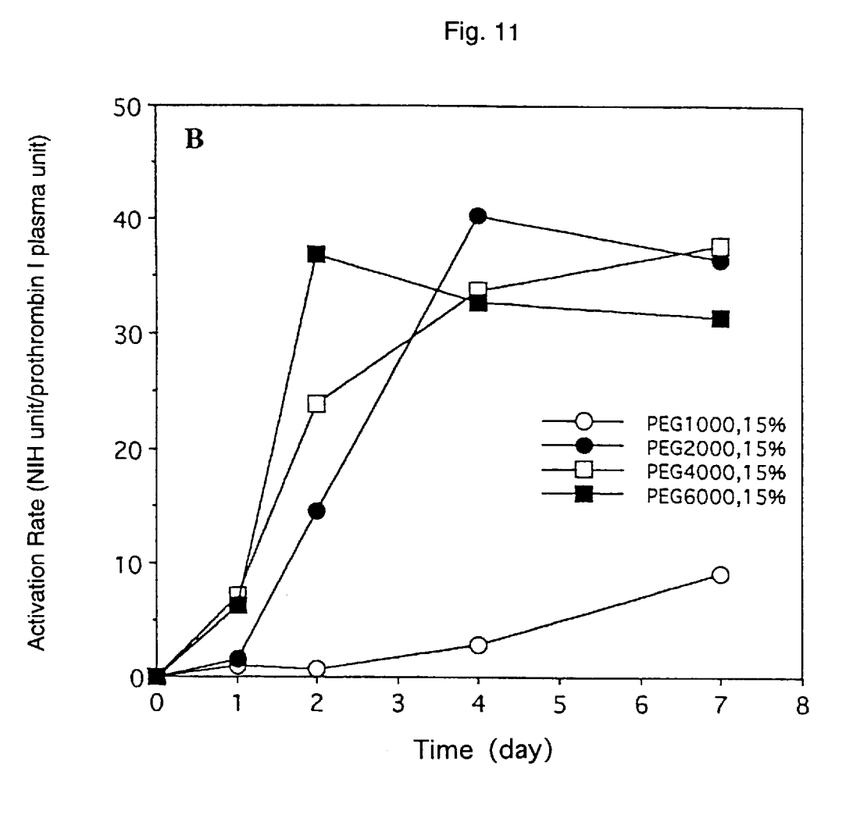
FIG. 11 shows effects of a molecular weight of PEG on the activation of prothrombin to thrombin in the presence of 15% PEG having various molecular weights.
Figure 12:
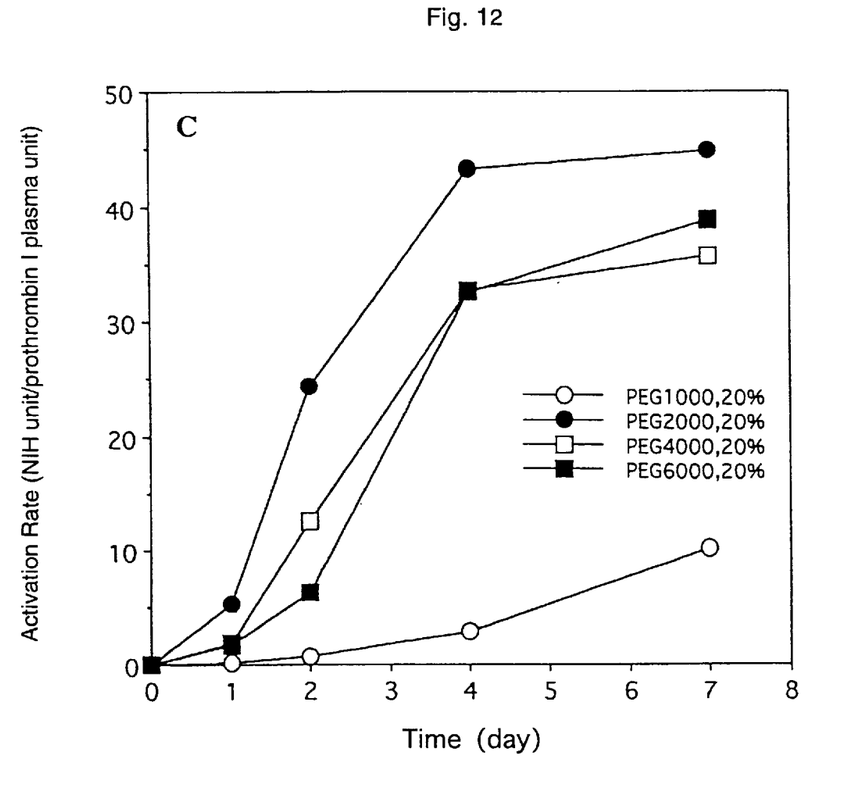
FIG. 12 shows effects of a molecular weight of PEG on the activation of prothrombin to thrombin in the presence of 20% PEG having various molecular weights.

The activation rate of prothrombin to thrombin by PEG treatment was studied with PEGs having various molecular weights. Using PEGs of various molecular weights (PEG 1,000, PEG 2,000, PEG 4,000 and PEG 6,000) at the concentration of 10%, 15% or 20%, prothrombin 22.8 plasma units/ml as prepared in Preparation 3, Factor X (120.5 μg/ml) and 5 mM calcium chloride were mixed together and the mixture was reacted at 25° C., pH 7.4. Activation rate of prothrombin to thrombin as a function of incubation time is shown in FIGS. 10 to 12.

With PEG 1,000, no significant enhancement of activation of prothrombin to thrombin was observed at any of PEG concentrations. When PEG 2,000 was used at the concentration of 10%, enhancement of activation was proved though slower than that with PEG 4,000 or PEG 6,000. With PEG 2,000 at the concentrations of 15% or 20%, enhancement of activation was comparable to that with PEG 4,000 or PEG 6,000. There was no significant distinction in enhancement of activation between PEG 4,000 and PEG 6,000.

Experiment 7

Figure 13:
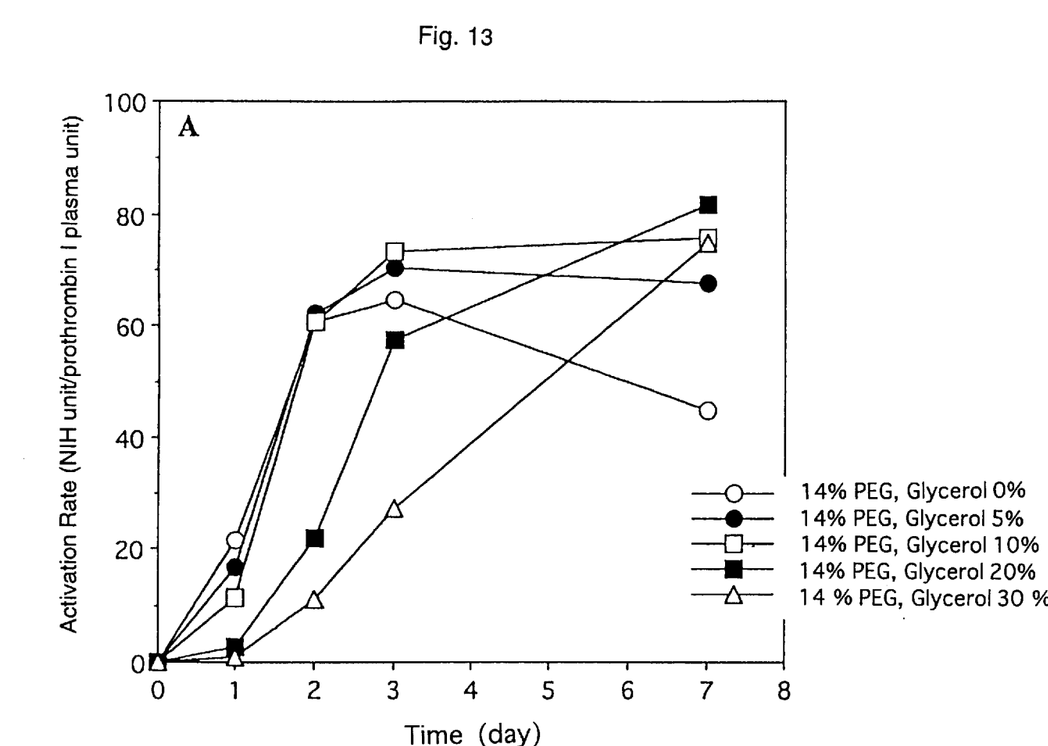
FIG. 13 shows effects of glycerol on the activation of prothrombin to thrombin enhanced by 14% PEG 4,000.
Figure 14:
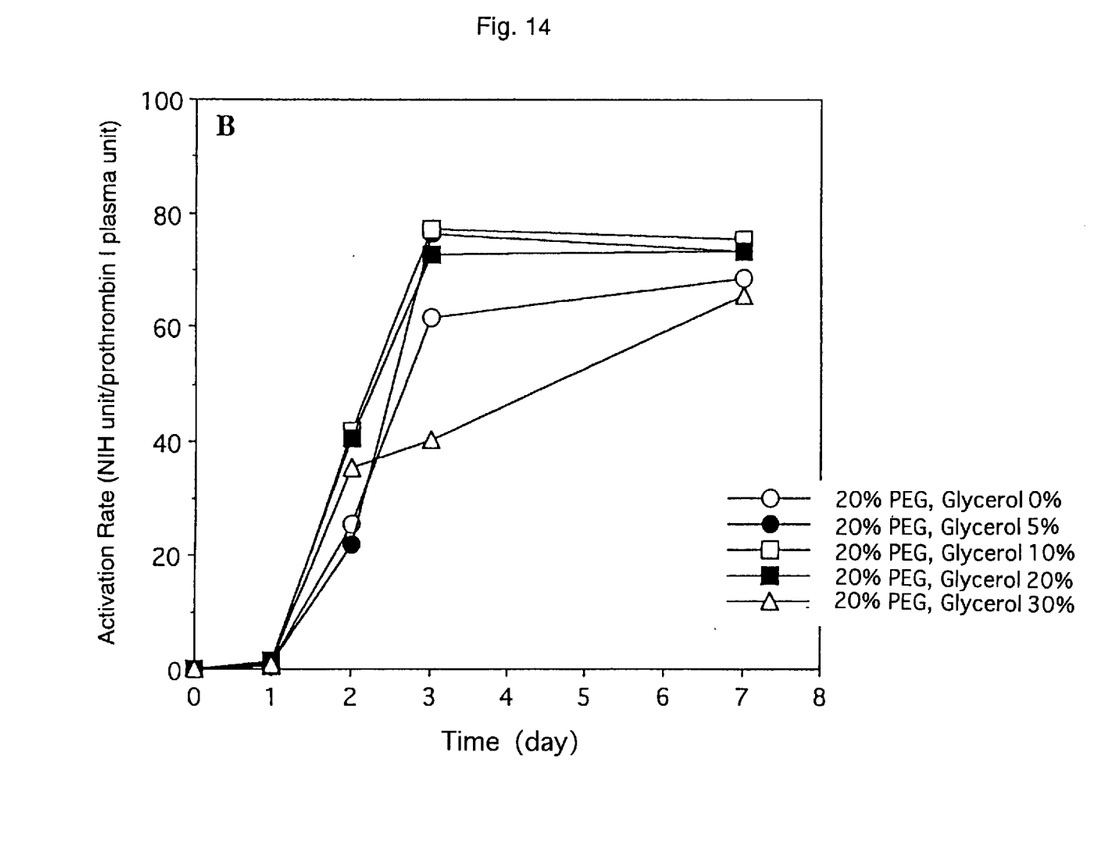
FIG. 14 shows effects of glycerol on the activation of prothrombin to thrombin enhanced by 20% PEG 4,000.

Effects of glycerol on the stability of thrombin formed in the activation of prothrombin by PEG treatment was studied. Using PEG 4,000 at the concentration of 14% or 20%, prothrombin 22.8 plasma units/ml as prepared in Preparation 3, Factor X (120.5 μg/ml), 5 mM calcium chloride and glycerol at various concentrations were mixed together and the mixture was reacted at 25° C., pH 7.4. Activation rate of prothrombin to thrombin as a function of incubation time is shown in FIGS. 13 and 14.

With 14% PEG 4,000, a maximum value of the activation rate was increased and decline in the activity as treatment was prolonged was repressed with glycerol at the concentration ranging from 5 to 30% as compared to the absence of glycerol. In case of 20% PEG 4,000, a maximum value of the activation rate was increased with glycerol at the concentration ranging from 5 to 20% as compared to the absence of glycerol.

EXAMPLE 1

Prothrombin and Factor X as prepared in Preparation 2 were concentrated with a ultrafiltration membrane and mixed with calcium chloride and PEG at a final concentration of 5 mM and 14%, respectively, and the mixture was reacted at 25° C. for 7 days.

Thrombin thus formed exhibited the activation rate of 48.4 (NIH units/prothrombin 1 plasma unit).

EXAMPLE 2

Thrombin as prepared in Example 1 was subjected to ultrafiltration/dialysis filtration using a ultrafiltration membrane and the solvent was replaced with 20 mM Tris-HCl, 0.15M NaCl, pH 8.0. This solution was adsorbed to SPTOYOPEARL (manufactured by TOSOH) equilibrated with the same buffer and washed to remove unbound proteins. A fraction containing thrombin was eluted with 20 mM $Na_3$ citrate, 0.5M NaCl, pH 6.0, concentrated, dialyzed, lyophilized, and heated.

What is claimed is:

1. A method for activating prothrombin to thrombin which comprises treating an aqueous solution containing prothrombin with polyethylene glycol.

2. The method for activating prothrombin to thrombin of claim 1 wherein treatment of said aqueous solution containing prothrombin with polyethylene glycol is conducted in the presence of a calcium salt.

3. The method for activating prothrombin to thrombin of claim 1 wherein said polyethylene glycol has a molecular weight ranging from about 2,000 to 6,000.

4. The method for activating prothrombin to thrombin of claim 1 wherein the final concentration of polyethylene glycol is 1 to 30% (w/v).

5. The method for activating prothrombin to thrombin of claim 2 wherein said calcium salt is selected from the group consisting of calcium chloride, calcium hydroxide and calcium acetate.

6. The method for activating prothrombin to thrombin of claim 2 wherein the final concentration of said calcium salt is 100 mM or less.

7. The method for activating prothrombin to thrombin of claim 6 wherein the final concentration of said calcium salt is 2 to 20 mM.

8. The method for activating prothrombin to thrombin of claim 1 wherein said aqueous solution containing prothrombin is a prothrombin complex.

9. The method for activating prothrombin to thrombin of claim 1 wherein said aqueous solution containing prothrombin is an aqueous solution containing mainly prothrombin and blood coagulation factor X.

10. A method for preparing thrombin which comprises activating prothrombin to thrombin by the method as set forth in claim 1, and isolating thrombin thus obtained.

11. The method for preparing thrombin of claim 12 which further comprises treating the thrombin with a cation exchanger for purification.

12. The method for activating prothrombin to thrombin of claim 1 wherein treatment of said aqueous solution containing prothrombin with polyethylene glycol is conducted in the absence of thromboplastin.

13. The method for activating prothrombin to thrombin of claim 1 wherein treatment of said aqueous solution containing prothrombin with polyethylene glycol is conducted in the presence of glycerol.

14. The method for activating prothrombin to thrombin of claim 1 wherein treatment of said aqueous solution containing prothrombin with polyethylene glycol is conducted at the temperature ranging from 4° to 37° C.

15. The method for activating prothrombin to thrombin of claim 14 wherein treatment of said aqueous solution containing prothrombin with polyethylene glycol is conducted at the temperature ranging from 10° to 25° C.

16. The method for activating prothrombin to thrombin of claim 2 wherein treatment of said aqueous solution containing prothrombin with polyethylene glycol is conducted in the absence of thromboplastin.

17. The method for activating prothrombin to thrombin of claim 16 wherein treatment of said aqueous solution containing prothrombin with polyethylene glycol is conducted in the presence of glycerol.

18. The method for activating prothrombin to thrombin of claim 17 wherein treatment of said aqueous solution containing prothrombin with polyethylene glycol is conducted at the temperature ranging from 4° to 37° C.

19. The method for activating prothrombin to thrombin of claim 18 wherein treatment of said aqueous solution containing prothrombin with polyethylene glycol is conducted at the temperature ranging from 10° to 25° C.

20. The method for activating prothrombin to thrombin of claim 19 wherein polyethylene glycol having a molecular weight ranging from about 2,000 to 6,000 is used at a final concentration of 1 to 30% (W/V), and said calcium salt is used at a final concentration of 100 mM or less.

* * * * *